(12) United States Patent
Xu et al.

(10) Patent No.: US 11,109,797 B2
(45) Date of Patent: Sep. 7, 2021

(54) PORTABLE ELECTRONIC DEVICE HAVING AN INTEGRATED BIO-SENSOR

(71) Applicant: Apple Inc., Cupertino, CA (US)

(72) Inventors: Qiliang Xu, Livermore, CA (US); Richard G. Huizar, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 536 days.

(21) Appl. No.: 15/942,499

(22) Filed: Mar. 31, 2018

(65) Prior Publication Data

US 2019/0069835 A1  Mar. 7, 2019

Related U.S. Application Data

(60) Provisional application No. 62/554,140, filed on Sep. 5, 2017.

(51) Int. Cl.
*A61B 5/024* (2006.01)
*A61B 5/026* (2006.01)
(Continued)

(52) U.S. Cl.
CPC ............ *A61B 5/443* (2013.01); *A61B 5/0059* (2013.01); *A61B 5/0205* (2013.01); *A61B 5/14551* (2013.01); *A61B 5/6898* (2013.01); *G06F 1/169* (2013.01); *G06F 1/1616* (2013.01); *G06F 1/1637* (2013.01); *G06F 1/1662* (2013.01); *G06F 1/1684* (2013.01);
(Continued)

(58) Field of Classification Search
CPC ..... A61B 5/443; A61B 5/0059; A61B 5/0205; A61B 5/14551; A61B 5/6898; A61B 5/021; A61B 5/024; A61B 5/02427; A61B 5/026; A61B 5/0816; A61B 5/14542; A61B 2560/0462; A61B 2562/0238; G06F 1/1616; G06F 1/1637; G06F 1/1662; G06F 1/1684; G06F 1/169; G06F 1/3231; G06F 1/3287
USPC ................................. 600/504–507
See application file for complete search history.

(56) References Cited

U.S. PATENT DOCUMENTS

| | | |
|---|---|---|
| 6,115,621 A | 9/2000 | Chin |
| 6,343,223 B1 | 1/2002 | Chin et al. |

(Continued)

FOREIGN PATENT DOCUMENTS

| | | |
|---|---|---|
| CN | 1493255 | 5/2004 |
| CN | 101427125 | 5/2009 |

(Continued)

*Primary Examiner* — Navin Natnithithadha
(74) *Attorney, Agent, or Firm* — Brownstein Hyatt Farber Schreck, LLP

(57) ABSTRACT

An electronic device includes a translucent layer that forms a portion of an exterior of the electronic device, an opaque material positioned on the translucent layer that defines micro-perforations, and a processing unit operable to determine information about a user via the translucent layer. The processing unit may be operable to determine the information by transmitting optical energy through a first set of the micro-perforations into a body part of the user, receiving a reflected portion of the optical energy from the body part of the user through a second set of the micro-perforations, and analyzing the reflected portion of the optical energy.

20 Claims, 11 Drawing Sheets

(51) Int. Cl.
*A61B 5/021* (2006.01)
*A61B 5/08* (2006.01)
*G06F 1/16* (2006.01)
*G06F 1/3287* (2019.01)
*G06F 1/3231* (2019.01)
*A61B 5/00* (2006.01)
*A61B 5/1455* (2006.01)
*A61B 5/0205* (2006.01)
*A61B 5/145* (2006.01)

(52) U.S. Cl.
CPC .......... *G06F 1/3231* (2013.01); *G06F 1/3287* (2013.01); *A61B 5/021* (2013.01); *A61B 5/024* (2013.01); *A61B 5/026* (2013.01); *A61B 5/02427* (2013.01); *A61B 5/0816* (2013.01); *A61B 5/14542* (2013.01); *A61B 2560/0462* (2013.01); *A61B 2562/0238* (2013.01)

(56) References Cited

U.S. PATENT DOCUMENTS

| | | | |
|---|---|---|---|
| 6,616,613 B1* | 9/2003 | Goodman | A61B 5/0002 600/504 |
| 6,927,844 B2 | 8/2005 | Higuchi et al. | |
| 7,822,469 B2 | 10/2010 | Lo | |
| 7,890,153 B2 | 2/2011 | Hoarau | |
| 7,978,332 B2 | 7/2011 | Wadman | |
| 8,005,624 B1 | 8/2011 | Starr | |
| 8,303,151 B2* | 11/2012 | Pance | H03G 3/32 362/606 |
| 8,437,825 B2* | 5/2013 | Dalvi | A61B 5/14551 600/344 |
| 8,577,431 B2* | 11/2013 | Lamego | A61B 5/6816 600/310 |
| 8,761,853 B2 | 6/2014 | Thaveeprungsriporn et al. | |
| 8,994,662 B2 | 3/2015 | Nakamura | |
| 9,060,700 B2 | 6/2015 | Cho et al. | |
| 9,161,722 B2* | 10/2015 | Besko | A61B 5/68335 |
| 9,314,197 B2 | 4/2016 | Eisen et al. | |
| 9,531,422 B2 | 12/2016 | Jang et al. | |
| 9,591,975 B2* | 3/2017 | Dalvi | A61B 5/70 |
| 9,620,312 B2 | 4/2017 | Ely et al. | |
| 9,622,694 B2* | 4/2017 | Mao | A61B 5/14553 |
| 9,717,425 B2* | 8/2017 | Kiani | A61B 5/02427 |
| 10,098,577 B2* | 10/2018 | Besko | A61B 5/14552 |
| 10,132,478 B2* | 11/2018 | Vasylyev | F21V 21/14 |
| 10,376,191 B1* | 8/2019 | Poeze | A61B 5/70 |
| 10,436,425 B1* | 10/2019 | Vasylyev | G02B 6/0068 |
| 10,537,271 B2* | 1/2020 | Mao | A61B 5/14553 |
| 10,656,714 B2* | 5/2020 | Ligtenberg | H03K 17/9647 |
| 10,758,179 B2 | 9/2020 | Bruekers et al. | |
| 10,830,421 B2* | 11/2020 | Vasylyev | F21V 9/08 |
| 10,871,828 B2* | 12/2020 | Ligtenberg | H01H 13/705 |
| 2003/0036685 A1* | 2/2003 | Goodman | A61B 5/021 600/300 |
| 2010/0004518 A1* | 1/2010 | Vo | A61B 5/70 600/310 |
| 2010/0004519 A1* | 1/2010 | Lamego | A61B 5/02416 600/310 |
| 2010/0010326 A1* | 1/2010 | Dalvi | A61B 5/1455 600/322 |
| 2011/0280042 A1* | 11/2011 | Pance | H03G 3/32 362/606 |
| 2013/0006074 A1 | 1/2013 | Pologe | |
| 2013/0060109 A1* | 3/2013 | Besko | A61B 5/14552 600/323 |
| 2013/0063972 A1* | 3/2013 | Pance | G02B 6/006 362/607 |
| 2013/0261407 A1 | 10/2013 | Koyama et al. | |
| 2013/0317370 A1* | 11/2013 | Dalvi | A61B 5/14552 600/476 |
| 2014/0066783 A1* | 3/2014 | Kiani | A61B 5/14546 600/476 |
| 2016/0022184 A1* | 1/2016 | Besko | A61B 5/14546 600/328 |
| 2016/0061726 A1 | 3/2016 | Ness et al. | |
| 2016/0070339 A1 | 3/2016 | Crawford et al. | |
| 2016/0378071 A1 | 12/2016 | Rothkopf | |
| 2017/0254518 A1* | 9/2017 | Vasylyev | F21V 21/14 |
| 2017/0325698 A1* | 11/2017 | Allec | A61B 5/7214 |
| 2018/0217668 A1* | 8/2018 | Ligtenberg | G06F 3/017 |
| 2018/0217669 A1* | 8/2018 | Ligtenberg | G06F 3/03547 |
| 2018/0218859 A1* | 8/2018 | Ligtenberg | G06F 3/04144 |
| 2019/0142287 A1* | 5/2019 | Boscke | A61B 5/02427 600/479 |

FOREIGN PATENT DOCUMENTS

| | | |
|---|---|---|
| CN | 101605495 | 12/2009 |
| CN | 103153172 | 6/2013 |
| CN | 103228205 | 7/2013 |
| CN | 104755020 | 7/2015 |
| CN | 105534513 | 5/2016 |
| CN | 105813554 | 7/2016 |
| WO | WO 99/039630 | 8/1999 |
| WO | WO 15/200386 | 12/2015 |
| WO | WO2016/040392 | 3/2016 |
| WO | WO 16/066888 | 5/2016 |
| WO | WO 16/166414 | 10/2016 |
| WO | WO 16/176218 | 11/2016 |

* cited by examiner

PORTABLE ELECTRONIC DEVICE HAVING AN INTEGRATED BIO-SENSOR

CROSS-REFERENCE TO RELATED APPLICATION(S)

This application is a nonprovisional patent application of and claims the benefit of U.S. Provisional Patent Application No. 62/554,140, filed Sep. 5, 2017 and titled "Portable Electronic Device Having an Integrated Bio-Sensor," the disclosure of which is hereby incorporated herein by reference in its entirety.

FIELD

The described embodiments generally relate to electronic devices and, more particularly, to determining a health metric or physiological condition using a bio-sensor that is integrated with the electronic device.

BACKGROUND

Portable electronic devices, including notebook computers, tablet computers, and mobile phones, have become common and useful devices. Many traditional portable electronic devices are configured to receive input using a keyboard or similar input device. However, few, if any, traditional notebook computers include sophisticated sensors or sensing techniques to monitor the user.

The present disclosure is directed to systems and techniques for integrating a bio-sensor into a surface of a portable electronic device.

SUMMARY

The present disclosure relates to body sensing via translucent layers with opaque layers. The electronic device includes an opaque layer positioned on a translucent layer that defines micro-perforations. A light source transmits light or other optical energy through the micro-perforations into a body part of a user. A light receiver receives the light that is reflected back from the body part of the user through the micro-perforations. Information about the user's body is determined from the light that is reflected back.

In some embodiments, a portable electronic device including an upper enclosure; a display positioned within the upper enclosure; a lower enclosure pivotally coupled to the upper enclosure and including a translucent layer defining an external surface and an opaque layer coupled to the translucent layer and defining an array of micro-perforations; a keyboard positioned within the lower enclosure; a bio-sensor positioned within the lower enclosure below the array of micro-perforations and including a light source operable to transmit light through the array of micro-perforations into a body part of a user and a light receiver operable to receive reflected light from the body part of the user; and a processing unit, communicably coupled to the light receiver and operable to determine a health metric based on the reflected light.

In various examples, the bio-sensor is positioned along a side of the keyboard and the body part is a palm of a hand of the user. In numerous examples, the light source is a green LED, the bio-sensor is configured to detect blood perfusion in the body part of the user and the health metric is at least one of a heart rate, a respiration rate, a blood oxygenation level, a blood volume estimate, or a blood pressure. In some examples, the light source is an infrared LED and the bio-sensor is configured to detect water content of the body part of the user.

In numerous examples, the array of micro-perforations are configured to obscure the light source and the light receiver when the bio-sensor is not in operation. In some examples, each micro-perforation of the array of micro-perforations is approximately 30-70 microns in diameter and is spaced approximately 80-500 microns apart from an adjacent micro-perforation.

In various examples, the translucent layer is at least one of glass or plastic and the opaque layer includes a layer of ink deposited on an internal surface of the translucent layer that is opposite to the external surface.

In various embodiments, an electronic device includes a translucent layer that forms a portion of an exterior surface of the electronic device, an opaque material positioned along an interior surface of the translucent layer that defines an array of micro-perforations, a light source positioned below the translucent layer and configured to transmit light through the array of micro-perforations, a light receiver positioned below the translucent layer proximate to the light source and configured to detect reflected light from a body part and a processing unit operable to determine bio-information based on the reflected light detected by the light receiver.

In some examples, the light source transmits the light through a first set of micro-perforations of the array of micro-perforations, the light receiver receives the reflected light through a second set of micro-perforations of the array of micro-perforations, the first set of micro-perforations extends along a first angle with respect to the exterior surface, and the second set of micro-perforations extends along a second angle with respect to the exterior surface that is different from the first angle. In such examples, the first set of micro-perforations may be angled toward the second set of micro-perforations.

In numerous examples, the light source transmits the light through a first set of micro-perforations of the array of micro-perforations, the light receiver receives the reflected light through a second set of micro-perforations of the array of micro-perforations, and the first set of micro-perforations is configured to direct the light along a non-perpendicular angle with respect to the exterior surface. In various examples, the light source transmits the light through a first set of micro-perforations of the array of micro-perforations, the light receiver receives the reflected light through a second set of micro-perforations of the array of micro-perforations, and the second set of micro-perforations is configured to receive light substantially aligned with a non-perpendicular angle with respect to the exterior surface and block light that is not substantially aligned with the non-perpendicular angle.

In some examples, the body part absorbs a portion of the light. The portion of the light absorbed by the body part may depend on a tissue density of the body part.

In numerous embodiments, a method of sensing a physiological condition includes while operating a bio-sensor in a first mode, detecting a proximity of a body part of a user with respect to an exterior surface of a translucent layer by producing a first light emission through the translucent layer; when the body part is proximate to the exterior surface of the translucent layer, operating the bio-sensor in a second mode by producing a second light emission through the translucent layer; and determining the physiological condition by analyzing a portion of the second light emission reflected from the body part.

In some examples, the first light emission of the first mode includes a non-visible light emission and the second light emission of the second mode includes a visible light emission. In various examples, an opaque layer is positioned along the translucent layer and defines an array of micro-perforations, the first and second light emissions are transmitted through the array of micro-perforations, and the opaque layer obscures the bio-sensor when the bio-sensor is operating in the first mode. In numerous examples, the bio-sensor uses power at a first rate while operating in the first mode, the bio-sensor uses power at a second rate while operating in the second mode, and the second rate is greater than the first rate.

In various examples, determining the physiological condition includes determining at least one of: a heart rate, a respiration rate, a blood oxygenation level, a blood volume estimate, or a blood pressure. In some examples, determining the physiological condition includes determining a photoplethysmogram for the user.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Figure 1A:
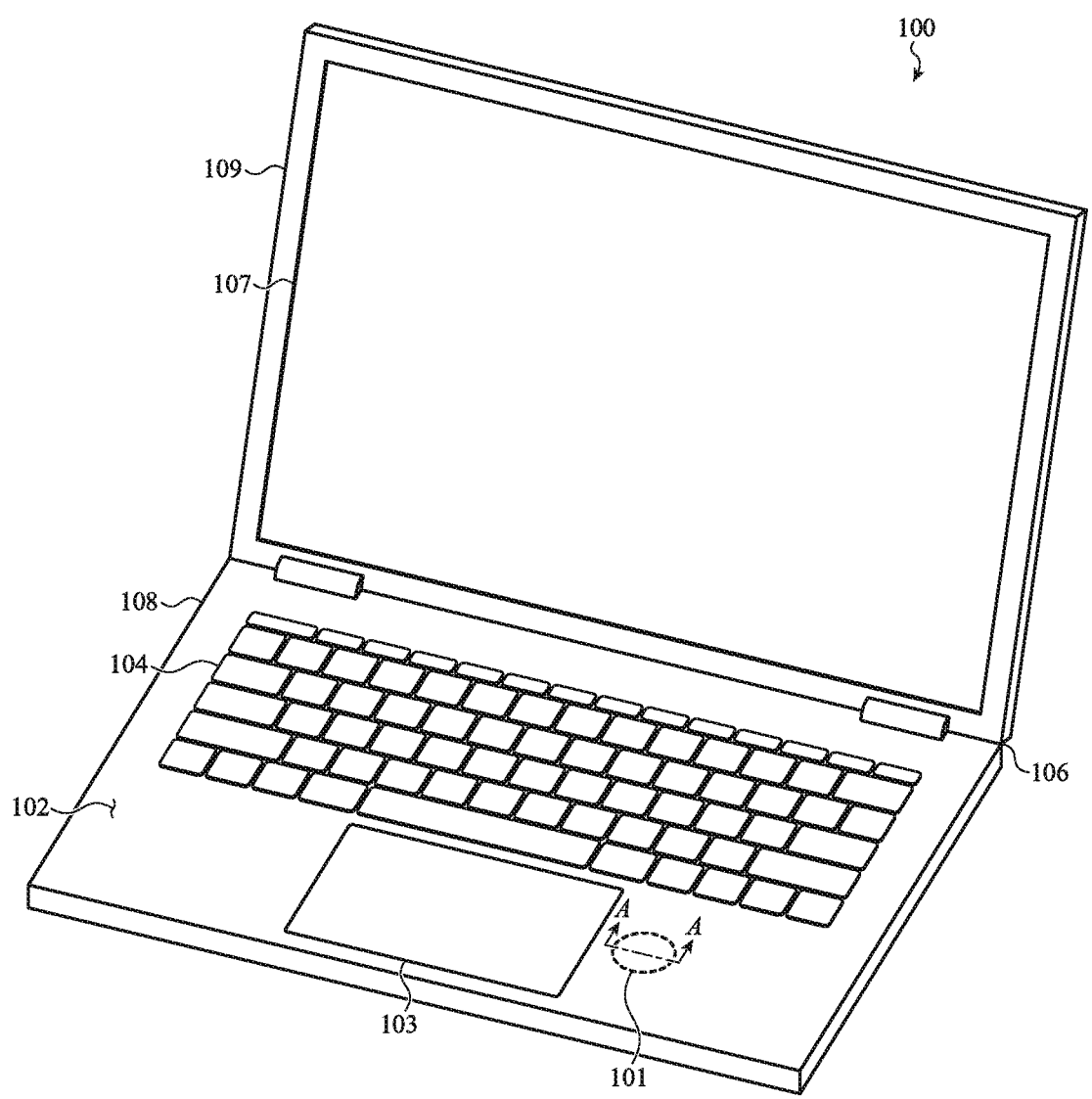
FIG. 1A depicts an example electronic device having an integrated bio-sensor.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The description that follows includes sample systems, apparatuses, methods, and computer program products that embody various elements of the present disclosure. However, it should be understood that the described disclosure may be practiced in a variety of forms in addition to those described herein.

The following disclosure relates to a bio-sensor that is integrated with an electronic device. In particular, the bio-sensor may be integrated into an enclosure of a notebook computer allowing the bio-sensor to measure a condition of the user while the device is in use. For example, the bio-sensor may be positioned adjacent to the keyboard along a region that corresponds to a location where a portion of the user's hand contacts the enclosure (e.g., the user's palm). As described herein, the enclosure may include a translucent layer or sheet that forms at least a portion of the exterior of the device. An opaque layer may be formed along an interior surface of the transparent layer and may define an array of micro-perforations that are able to transmit light from the sensor but also obscure the bio-sensor from the user when it is not in operation.

In some embodiments, the bio-sensor is configured to produce a light emission that is transmitted through the micro-perforations defined in the opaque layer. In an example mode of operation, the bio-sensor may be used to determine a health metric or a physiological condition by detecting the light that is reflected off the body part of a user (e.g., the palm of a user's hand). In another example mode of operation, the bio-sensor may be used to detect a proximity of the user's hand with respect to the device. In response to the user's hand being detected as proximate to the bio-sensor, the device may be configured to change operation of the bio-sensor, alter the operational state of the device, or perform some other function.

The bio-sensor may include a variety of different light sources that transmit the light and/or a variety of different light receivers that receive the light. For example, the light may be transmitted by a light emitting diode (LED), a micro-LED, an organic light emitting diode (OLED), or other type of light source. The light source may be configured to emit a visible light emission (e.g., green or red) or a non-visible light emission (e.g., infrared or ultraviolet). The light may be received by a photodiode, photo-sensor, or other of light receiver.

In some cases, a portion of the exterior of the device enclosure is defined by a translucent layer or substrate. For example, the upper surface of a notebook enclosure may be defined by the translucent layer, which may include one or more sheets of translucent material. The translucent layer may be formed of any translucent layer or translucent material including, for example, glass, sapphire, plastic, and so on. An opaque layer may be formed or positioned along an interior surface of the translucent layer to mask or visually obscure internal components of the device. The opaque layer may be any opaque layer or opaque material, such as paint, ink, and so on. The opaque layer may reduce or prevent the visibility of the bio-sensor components from the outside of the enclosure while allowing light to pass through the micro-perforations to perform the sensing operations. The opaque layer may also help direct the light along a particular direction to assist with sensing and/or optical noise reduction.

The micro-perforations may be formed with a variety of different dimensions. The diameter or size of each perforation and the may be sufficiently small that the opaque layer blocks or obscures the visibility internal components and may also not be visually distinguishable from a portion of the opaque layer not having micro-perforations. At the same time, the diameter or size of each perforation may be sufficiently large to allow sensor light to pass to enable operation of the bio-sensor. The spacing or arrangement of the micro-perforations may also be adapted to achieve this functionality. For example, the micro-perforations may be approximately 30-70 microns across and may be spaced at least approximately 80-500 microns apart. In some implementations, the micro-perforations may be angled transverse with respect to the translucent layer. The angle of micro-perforations may determine a transmission direction or a receiving direction of the light passing through the translucent layer.

The above transmission and receiving of light through the micro-perforations defined in the opaque layer on the translucent layer may be used to implement a variety of different sensors in an electronic device. Examples of such sensors include, but are not limited to, bio-sensors (e.g., health sensors, photoplethysmography (PPG) sensors), ambient light sensors, proximity sensors, infrared distance sensors, and so on. In some implementations, the electronic device may a single sensor to perform different sensing functions. For example, the device may be configured to operate the sensor in a first mode to detect the proximity of the user with respect to the device and to operate the same sensor in another mode to sense a physiological condition or determine a health metric associated with the user. In one example, the sensor may be used to adjust power levels of the electronic device (e.g., to switch an input and/or output component from a low power state to an active state) when the sensor detects that a user has moved into a position to use the electronic device. The sensor may also be used to illuminate an input device when the sensor detects that a user has moved into a position to use the input component. The same sensor may be operated in a different, bio-sensing mode to detect health information about a user (e.g., determine a heart rate for the user, a photoplethysmogram for the user, and so on). A variety of different configurations and uses are possible and contemplated without departing from the scope of the present disclosure.

As described herein, the translucent (e.g., light transmissible) layer may be formed from one or more translucent materials including, for example, glass, ceramic, plastic, or a combination thereof. As used herein, the term translucent or translucent layer may be used to refer to a material or layer that allows the passage of light and does not require that the material or layer be transparent, clear, or otherwise free from features that scatter or absorb some amount of light. As used herein, the term translucent may generally refer to a material or layer that is optically transparent, partially, transparent, or otherwise able to transmit light.

These and other embodiments are discussed below with reference to FIGS. 1-10. However, those skilled in the art will readily appreciate that the detailed description given herein with respect to these Figures is for explanatory purposes only and should not be construed as limiting.

FIG. 1A depicts an example electronic device 100 that includes a bio-sensor. In particular, the electronic device 100 includes a bio-sensor or other type of sensor that is operable to sense a user through a translucent layer 102. The translucent layer 102 may define an exterior surface of the device and area 101 along the exterior surface may correspond to the location of the bio-sensor that is positioned within the lower enclosure 108. The bio-sensor may be configured to transmit light or other optical energy through micro-perforations defined in an opaque layer on the translucent layer 102 and receive a portion of the light back through the micro-perforations reflected back from the body part of a user.

Figure 1B:
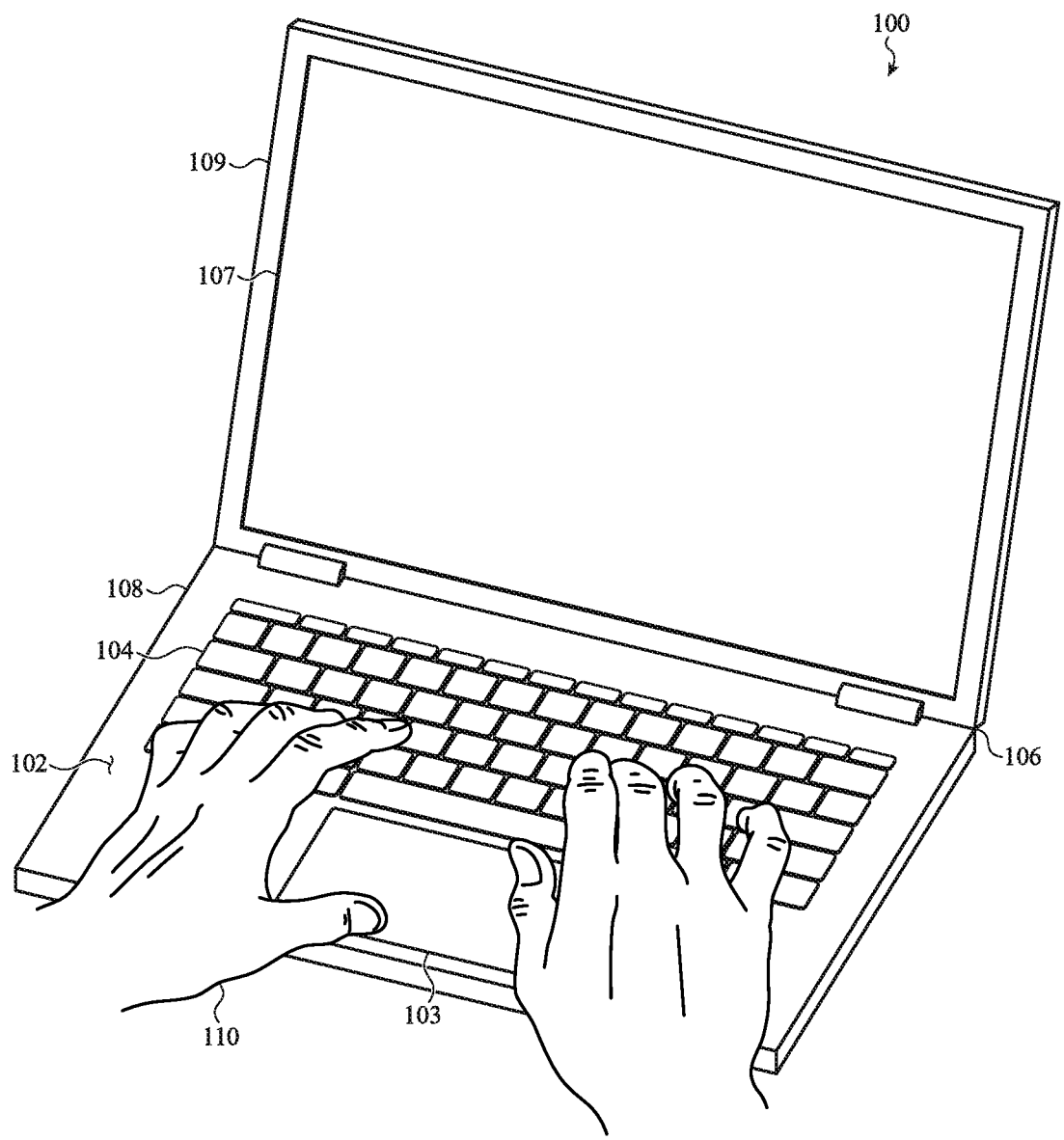
FIG. 1B depicts the example electronic device of FIG. 2 while the user is using a keyboard.

FIG. 1B illustrates a body part of the user 110 (e.g., a user's hand) in a position associated with the use of the device 100. In particular, the body part of the user 110 is positioned such that at least a portion (e.g., the user's palm) is contacting the lower enclosure 108 along the area 101. As described in more detail below with respect to FIG. 6, the bio-sensor may be configured to measure a property or condition of the body part of the user 110, which may be used to determine a physiological condition or health metric. In accordance with some embodiments, the bio-sensor may also be operated in a proximity sensor mode to detect the presence or absence of the body part of the user 110.

As shown in FIGS. 1A and 1B, the electronic device 100 includes an upper enclosure 109, a display 107 positioned within the upper enclosure 109, a lower enclosure 108 pivotally coupled to the upper enclosure via a hinge 106. The lower enclosure 108 may include the translucent layer 102 defining an exterior surface of the device 100. An opaque layer may be positioned along an interior surface of the translucent layer 102 and define an array of micro-perforations (which are described in detail below with respect to FIG. 2). A bio-sensor may be positioned within the lower enclosure 108. The micro-perforations may obfuscate and/or otherwise hide the bio-sensor from view.

The bio-sensor may include an optical energy source, such as a light source, operable to transmit light through the micro-perforations into the body part of the user 110. The bio-sensor may also include an optical energy receiver, such as a light receiver, operable to receive reflected light from the body part of the user 110. The electronic device may further include a processing unit, communicably coupled to the light receiver and operable to determine a physiological condition (i.e., information about the body part of the user 110) based on the reflected light.

As shown in FIGS. 1A and 1B, a keyboard 104 and trackpad 103 may be positioned within the lower enclosure 108. The keyboard 104 may include an electromechanical keyboard, virtual keyboard, or other type of keyboard component/device configured to receive keystrokes from the user. The trackpad 103 may be an electromechanical trackpad, an electronic trackpad, virtual trackpad, or other touch-sensitive device configured to receive touch and/or force input from the user. The bio-sensor may be positioned below (e.g., adjacent) the keyboard 104 and along a side of the trackpad 103. As stated previously, the location of the bio-sensor may correspond to a predicted location of the user's palm during a normal or predicted typing position.

In various implementations, the transmission and receiving of light through the micro-perforations may be used to implement a variety of different sensors or sensing modes for the electronic device 100. In various examples, these sensors or sensing modes include, but are not limited to, health sensors, ambient light sensors, proximity sensors, infrared distance sensors, PPG sensors, and so on. The electronic device 100 may use one or more of these sensors or sensing modes in a variety of different ways.

In one example, the electronic device 100 may transmit and receive light through the micro-perforations to implement a proximity sensor. The proximity sensor may detect that the body part of the user 110 is proximate to the area 101 when a portion of transmitted light is reflected and received. To the contrary, if the body part of the user 110 is not sufficiently close to the area 101, the body part of the user 110 may not receive and/or reflect any portion of the transmitted light. If a portion of transmitted light is not reflected and received, the electronic device may determine that the body part of the user 110 is not proximate to the area 101. In some implementations, a distance from the area 101 to the body part of the user 110 may be determined based on the amount of time between transmission and receiving of the light, indicating the amount of time taken by the light to travel from the area 101 to the body part of the user 110 and back again.

As shown in FIG. 1A, the area 101 of the translucent layer 102 corresponding to the sensor may be positioned adjacent to input devices such as the trackpad 103 and/or the keyboard 104. As such, when the user 110 is positioned to use the input devices, the proximity of the body part of the user 110 may be detected when the bio-senor is operated as a proximity sensor or in a proximity-sensing mode. In some implementations, the electronic device 100 may be configured to use such a proximity sensor to determine to adjust power levels of the electronic device 100. For example, the electronic device 100 may switch components, such as the trackpad 103, the keyboard 104, and/or a display 107, in a low power state (such as a powered down state) in order to conserve power or battery life when the electronic device 100 is not in use. The electronic device 100 may determine that the electronic device 100 is not in use when the proximity detector has not detected the body part of the user 110 for a period of time, such as five minutes. When the proximity sensor detects the body part of the user 110 while the electronic device 100 is operating in the low power state, the electronic device may switch from the low power state to an active state. For example, the electronic device 100 may activate a component, such as the trackpad 103, the keyboard 104, and/or a display 107. In another example implementation, the electronic device 100 may be configured with a light source operable to illuminate an input device, such as the trackpad 103 and/or the keyboard 104. In order to conserve power or battery life, or to be less obtrusive, the electronic device 100 may illuminate the input device when the proximity sensor detects that the user's body part is in position to use the input device.

By way of another example, the bio-sensor may transmit and receive light through the micro-perforations to measure a property or condition of the user 110 and used to determine a physiological condition or health metric. When light is transmitted into the body part of the user 110, the body part of the user 110 may absorb a portion of the light. The portion of the light that is not absorbed by the body part of the user 110 may be reflected back. The portions of the light that are absorbed or reflected by the body part of the user 110 may be dependent on the tissue density (or other density) of portions of the body part of the user 110. This may be used to measure, water content, perfusion, blood flow, and/or other health-related characteristics of the user 110. The electronic device 100 may use the bio-sensor to determine a heart rate for the user 110, a blood pressure for the user 110, a blood perfusion in the user 110, a water content of the user 110, a blood oxygenation level of the user, a blood volume estimate for the user 110, a respiration rate of the user 110, a photoplethysmogram for the user 110, and so on.

As shown in FIGS. 1A and 1B, the area 101 of the translucent layer 102 corresponding to the sensor may be positioned adjacent to input devices such as the trackpad 103 and/or the keyboard 104. As such, when the user 110 is positioned to use the input devices, the body part of the user 110 may be positioned to be detected by the bio-sensor. The electronic device 100 may thus use the bio-sensor to discreetly monitor health information about the user 110 while the user is operating the electronic device 100 without forcing the user to specifically move into a position for monitoring. The electronic device 100 may continuously, periodically, and/or otherwise monitor the health information. The electronic device 100 may also communicate with one or more other electronic devices (such as an associated cellular telephone, wearable device, and so on) to monitor, process, store, and/or take various actions based on such health information.

In some implementations, the bio-sensor may determine health information about the user 110 by transmitting and receiving multiple wavelengths of light. For example, the bio-sensor may transmit and receive green and red light. Different substances and/or colored materials may absorb light differently. For example, green, red, and/or infrared light may be absorbed differently by darker hair, tattoos, and so on. By determining health information by comparing multiple wavelengths of light that have been transmitted and reflected back by the body part of the user 110, the electronic device 100 may determine more accurate health information than might be possible by using a single wavelength of light.

In another example, the electronic device may utilize different sensors and/or different sensing modes having different wavelengths of light in different combinations. For example, the bio-sensor functioning as proximity sensor or in a proximity-sensing mode may use infrared light or another non-visible light source. When the bio-sensor is functioning as health sensor or in a health-sensing mode, the bio-sensor may use light in the visible spectrum. To prevent the light in the visible spectrum from being noticed by the user 110, the electronic device 100 may first operate the bio-sensor in a proximity-sensing mode to detect the body part of the user 110 as the infrared light may not be visually discernible to the user. Once the electronic device 100 determines that the bio-sensor is covered by the body part of the user 110, the electronic device 100 may then cause the bio-sensor to operate in a health-sensing mode using visible light.

Further, in various examples, an electronic device may operate the bio-sensor in a proximity-sensing mode to guide the user 110 to an optimal position for operating the bio-sensor in a health-sensing mode. For example, health information such as heart rate or blood pressure may be most accurately detected optically from the palm of the hand. As such, the electronic device 100 may determine where the user's hand is with respect to the health sensor and may provide output to the user 110 to direct the user 110 to move his hand until it is in an optimal position for operating the bio-sensor in a health-sensing mode.

In still other examples, the electronic device 100 may operate the bio-sensor as an ambient light sensor or in an ambient light-sensing mode. When operating in an ambient light-sensing mode, the bio-sensor may be configured to detect ambient (e.g., sunlight or visible light) to determine an ambient light level of an environment in which the electronic device 100 is present. The electronic device 100 may also use the ambient light-sensing mode to determine proximity of the user, as the ambient light sensor may not receive ambient light if blocked by the body part of the user 110.

Although a single sensor is described above as corresponding to the area 101 of the translucent layer 102, it is understood that this is an example. In various implementations, the electronic device 100 may include any number of sensors that correspond to any number of different areas of the translucent layer 102. Various configurations are possible and contemplated. For example, the area 101 is illustrated as being positioned to the right of the trackpad 103 in FIG. 1A, as shown. In some implementations, a second sensor may correspond to an additional area of the translucent layer 102 that is positioned to the left of the trackpad to mirror the area 101.

As illustrated in FIGS. 1A and 1B, the electronic device 100 may be a laptop or notebook computing device. However, it is understood that this is an example and that in other implementations the electronic device 100 may be any electronic device, such as a desktop computing device, a tablet computing device, a wearable device, a smart phone, a digital media player, a display, a printer, a kitchen appliance, a cellular telephone, a mobile computing device and so on.

The electronic device 100 may include a variety of components, shown or not shown. For example, the electronic device 100 may include a variety of different components such as one or more communication components, one or more non-transitory storage media (which may take the form of, but is not limited to, a magnetic storage medium; optical storage medium; magneto-optical storage medium; read only memory; random access memory; erasable programmable memory; flash memory; or the like), and so on without departing from the scope of the present disclosure. Various configurations are possible and contemplated.

Figure 2:
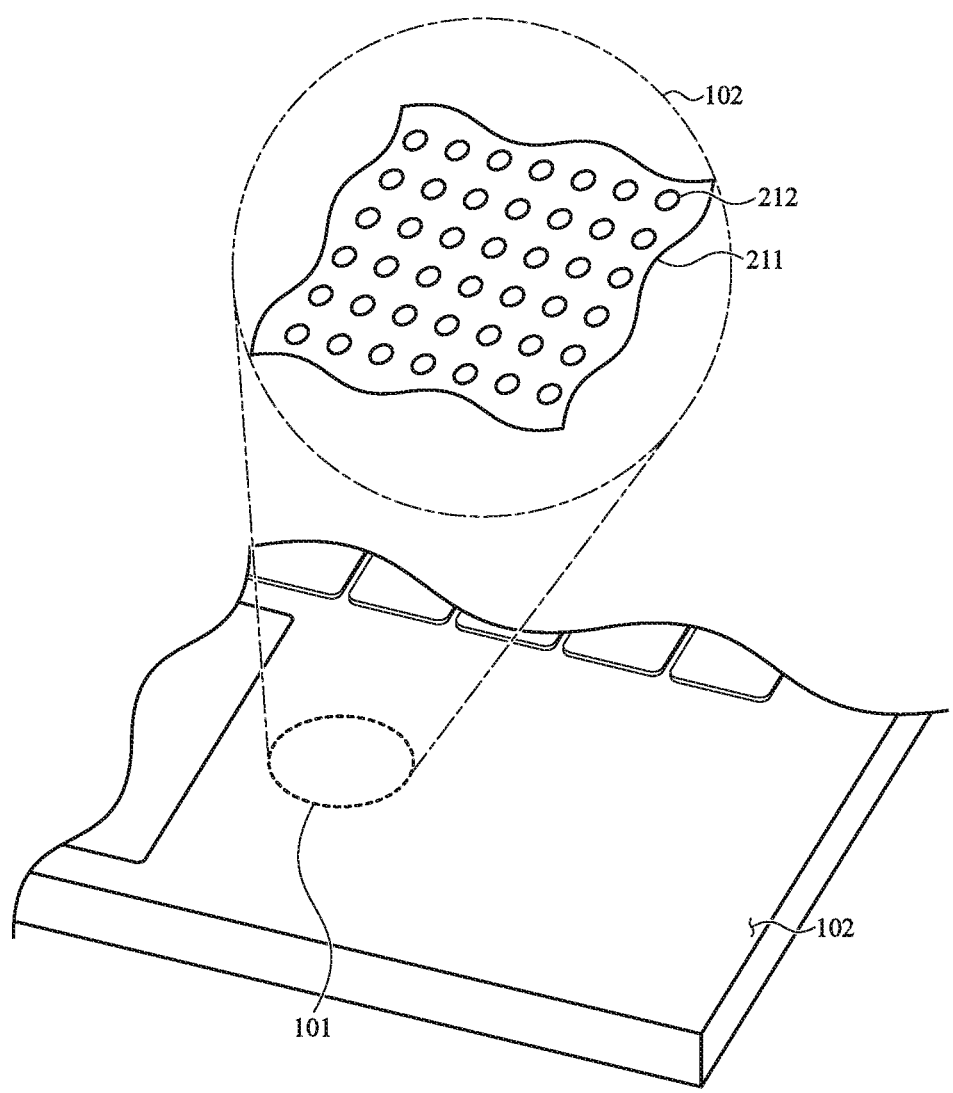
FIG. 2 depicts a detail view of a sensing area of the electronic device.

FIG. 2 depicts a detail view of the area 101 of the translucent layer 102 corresponding to the sensor. The translucent layer 102 may be formed of any kind of translucent layer or translucent material, such as glass, plastic, and so on. An opaque layer 211 may be formed on the translucent layer 102. The opaque layer 211 (which may be any opaque layer or opaque material, such as light reflective, absorptive, or blocking paint, ink, and so on) may define a array or set of micro-perforations 212.

The opaque layer 211 may be visible through the translucent layer and may visually obscure or block the viewing of internal components through the translucent layer 102. The opaque layer 211 may also prevent light that does not pass through the micro-perforations 212 from being visible through the translucent layer. The opaque layer 211 may be positioned on an exterior portion of the translucent layer 102, an interior portion of the translucent layer 102, within the translucent layer 102, and so on. In implementations where the opaque layer 211 is positioned along an interior surface of the translucent layer 102 and/or within the translucent layer 102, the opaque layer 211 may be visible through the translucent layer 102.

The micro-perforations 212 may be configured in a variety of different arrangements and with a variety of different dimensions. (The size and spacing of the micro-perforations 212, 312 depicted in FIGS. 2 and 3 may be exaggerated for purposes of illustration and may not be representative or drawn to scale.) The dimensions may be sufficiently small that the opaque layer 211 blocks internal components and/or light that does not passing through the micro-perforations 212 from being visible through the translucent layer 102 while light is still able to pass through the micro-perforations 212. In one example configuration, the micro-perforations 212 may have a size or diameter of approximately 30-70 microns. While the micro-perforations 212 are depicted as being circular in shape, the shape may vary depending on the implementation and may include other shapes including, rectilinear shapes, curved shapes, slits, and so on. The micro-perforations 212 may be spaced approximately 80-500 microns apart. Stated another way, each micro-perforation may approximately 80-500 microns from an adjacent micro-perforation.

Figure 3:
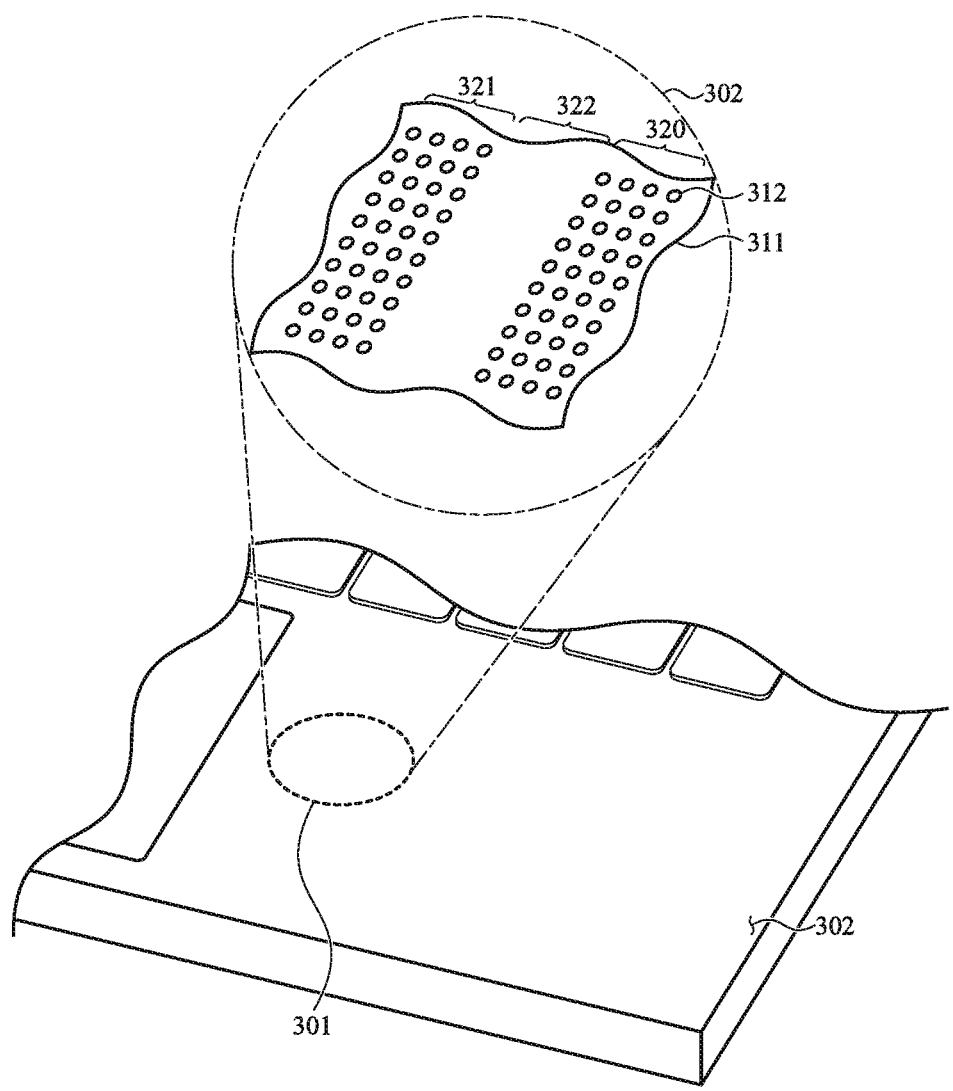
FIG. 3 depicts an alternative implementation of FIG. 2 where the opaque layer defines a micro-perforated transmission region and a micro-perforated receiving region.

FIG. 2 illustrates a uniform arrangement of the micro-perforations 212. In some examples, the electronic device 100 may use the same micro-perforations 212 for transmitting and receiving light. In other implementations, the electronic device 100 may use a first set of the micro-perforations 212 for transmitting light and a second set of the micro-perforations 212 for receiving light. In still other implementations, transmitting and receiving areas of micro-perforations 212 may be separated For example, FIG. 3 depicts an alternative implementation of the area 301 of the translucent layer 302 corresponding to the sensor of FIG. 2 where the opaque layer 311 defines a micro-perforation transmission region 320 and a micro-perforation receiving region 321. In this implementation, a first set of the micro-perforations 312 defined in the micro-perforation transmission region 320 may be used for transmitting light and a second set of the micro-perforations 312 defined in the micro-perforation receiving region 321 may be used for receiving light. Further, the opaque layer 311 may also include a separation region 322 between the micro-perforation transmission region 320 and the micro-perforation receiving region 321 that does not define micro-perforations 312.

Figure 4:
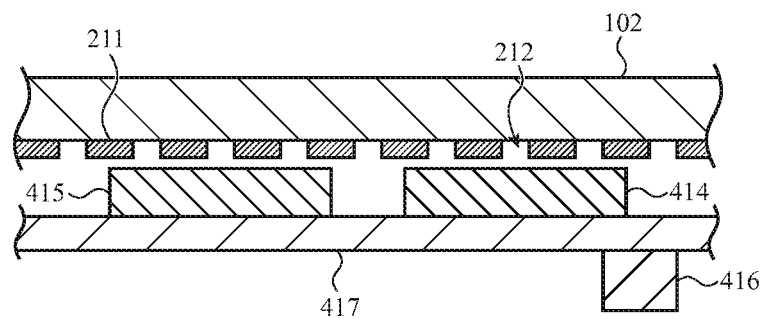
FIG. 4 depicts a cross-sectional view of the sensing area, taken along section A-A of FIG. 1A.

FIG. 4 depicts a cross-sectional view of the area 101 of the translucent layer 102 corresponding to the sensor, taken along line A-A of FIG. 1A. In this implementation, a bio-sensor may include an optical energy source, such as a light source 414 (such as an LED, an OLED, an incandescent light source, and/or other light source), configured to transmit light or other optical energy through the translucent layer 102 via one or more of the micro-perforations 212. Similarly, the bio-sensor may include an optical energy receiver, such as a light receiver 415 (such as a photodiode and/or other image or light sensor), configured to receive light through the translucent layer 102 via one or more of the micro-perforations 212. The light source 414 may transmit the light through the translucent layer 102 via one or more of the micro-perforations 212 into a body part of a user. Similarly, the light receiver 415 may receive light through the translucent layer 102 via one or more of the micro-perforations 212, such as a portion of the light transmitted by the light source 414 after it is reflected back by the body part of the user.

The light source 414 and the light receiver 415 may be connected to a processing unit 416 and/or other processor or controller via one or more electrical connections, such as a substrate 417 which may be a printed circuit board or similar component that provides structural support to the light source 414 and the light receiver 415. The processing unit 416 may control light transmission by the light source 414, light receiving by the light receiver 415, determination of information about the body of the user based on light received by the light receiver 415, and so on.

Thus, as shown, the electronic device 100 may include a translucent layer 102 defining an external surface, an opaque layer 211 coupled to the translucent layer 102 and defining an array of micro-perforations 212, and a bio-sensor positioned below the array of micro-perforations 212. The bio-sensor may include a light source 414 operable to transmit light through the array of micro-perforations 212 into a body part of a user and a light receiver 415 operable to receive reflected light from the body part of the user. Further, the electronic device 100 may include a processing unit 416, communicably coupled to the light receiver 415 and operable to determine a health metric based on the reflected light.

Further as shown, the electronic device 100 may include a translucent layer 102 that forms a portion of an exterior surface of the electronic device 100, an opaque material 211 positioned along an interior surface of the translucent layer 102 that defines an array of micro-perforations 212, a light source 414 positioned below the translucent layer 102 and configured to transmit light through the array of micro-perforations 212, and a light receiver 415 positioned below the translucent layer 102 proximate to the light source 414 and configured to detect reflected light from a body part. The electronic device 100 may also include a processing unit 416 operable to determine bio-information based on the reflected light detected by the light receiver 415.

FIG. 4 illustrates the micro-perforations 212 as angled orthogonal or perpendicular to the translucent layer 102. In various implementations, the micro-perforations 212 may be arranged along a non-perpendicular angle to direct transmission and/or receiving of light.

Figure 5:
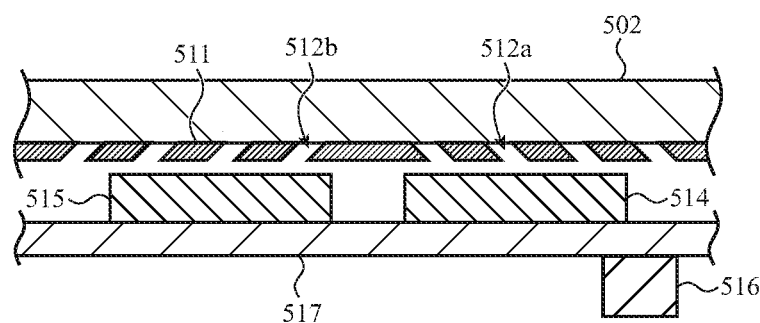
FIG. 5 depicts a cross-sectional view of another embodiment of the sensing area taken along section A-A including micro-perforations that are angled transverse to a sensing surface.

For example, FIG. 5 depicts an alternative implementation of FIG. 4 where the micro-perforations 512 are arranged along a non-perpendicular angle with respect to an exterior surface of the translucent layer 502. The angle of the micro-perforations 512 may determine a transmission direction and/or a receive direction of the light or other optical energy passing through the translucent layer 502.

As shown in FIG. 5, the micro-perforations 512A associated with the light source 514 are angled differently than the micro-perforations 512B associated with the light receiver 515. Specifically, the micro-perforations 512A extend along a first angle with respect to the exterior surface, which is a mirror of the micro-perforations 512B that extend along a second angle with respect to the exterior surface. Stated another way, the micro-perforations 512A associated with the light source 514 are angled transverse to the translucent layer 502 (and/or the substrate 517) and toward the micro-perforations 512B associated with the light receiver 515, and vice versa. Thus, the micro-perforations 512A associated with the light source 514 may direct the light or light emission along the non-perpendicular angle shown. Similarly, the micro-perforations 512B associated with the light receiver 515 may be configured to receive light substantially aligned with a non-perpendicular angle with respect to the exterior surface and block light that is not substantially aligned with the non-perpendicular angle. This may improve receiving and reflection of the light by a body part of the user and/or receiving of light reflected by the body part of the user.

Thus, as shown, an electronic device may include a translucent layer 502 defining an external surface, an opaque layer 511 coupled to the translucent layer 502 and defining an array of micro-perforations 512A, 512B, and a bio-sensor positioned below the array of micro-perforations 512A, 512B. The bio-sensor may include a light source 514 operable to transmit light through the array of micro-perforations 512A into a body part of a user and a light receiver 515 operable to receive reflected light from the body part of the user. Further, the electronic device 100 may include a processing unit 516, communicably coupled to the light receiver 515 and operable to determine a health metric based on the reflected light.

Further as shown, an electronic device may include a translucent layer 502 that forms a portion of an exterior surface of the electronic device, an opaque material 511 positioned along an interior surface of the translucent layer 502 that defines an array of micro-perforations 512A, 512B, a light source 514 positioned below the translucent layer 502 and configured to transmit light through the array of micro-perforations 512A, and a light receiver 515 positioned below the translucent layer 502 proximate to the light source 514 and configured to detect reflected light from a body part. The electronic device may also include a processing unit 516 operable to determine bio-information based on the reflected light detected by the light receiver 515.

Figure 6:
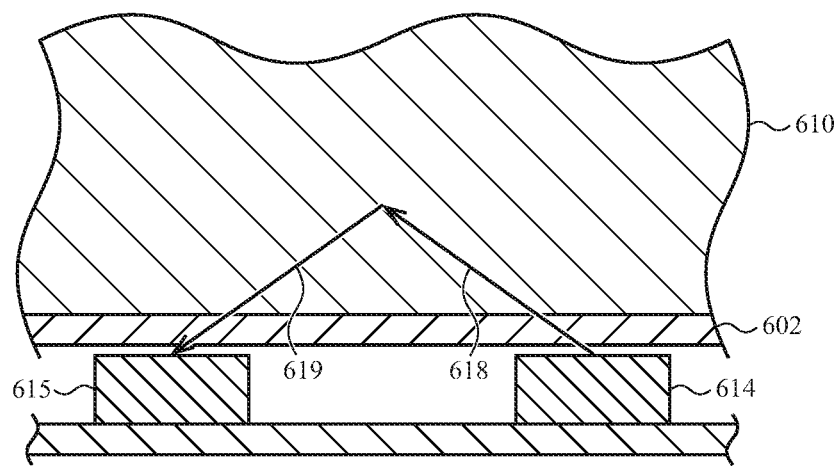
FIG. 6 depicts an optical schematic of a bio-sensor integrated with an electronic device.

FIG. 6 depicts a simplified process of detecting information about a body 610 using optical energy 618, 619 (such as light). An optical energy source, such as a light source 614, may transmit optical energy 618 through a translucent layer 602 into a body 610. The body 610 may absorb a portion of the optical energy 618. The portion of the optical energy 618 not absorbed by the body 610 may be reflected 619 back to an optical energy receiver, such as a light receiver 615, through the translucent layer 602. The portions of the optical energy 618 that are absorbed or reflected 619 by the body 610 may be dependent on the tissue density (or other density) of portions of the body 610 and may be used to measure blood flow and/or other health-related characteristics of the body 610.

In various implementations, a bio-sensor may utilize this process of detecting physiological information (i.e., health-related information, physiological condition, or other information about a body 610) to calculate a health metric or other health-related information. For example, physiological information may include, but is not limited to, the physiological conditions of heart rate, respiration rate, blood oxygenation level, blood volume estimate, blood pressure, and so on. Such a sensor may be implemented in the electronic device 100 of FIGS. 1A-1B.

As one example, an electronic device may include an array of light sources 614 and a detector or other light receiver 615 that are configured to function as an optical sensor or sensors. In one example, an optical sensor or sensors may be implemented as a pairing of one or more light sources 614 and the light receiver 615. In one example implementation, the light receiver 615 may be configured to collect light and convert the collected light into an electrical sensor signal that corresponds to the amount of light incident on a surface of the light receiver 615. In one embodiment, the light receiver 615 may be a photodetector, such as a photodiode. In other embodiments, the light receiver 615 may include a phototube, photosensor, or other light-sensitive device.

In some cases, the one or more bio-sensors may operate as a PPG sensor or sensors. In some instances, a PPG sensor is configured to measure light and produce a sensor signal that can be used to estimate changes in the volume of a part of a user's body. In general, as light from the one or more light sources 614 passes through the user's skin and into the underlying tissue, some light is reflected, some is scattered, and some light is absorbed, depending on what the light encounters. The light that is received by the light receiver 615 may be used to generate a sensor signal, which may be used to estimate or compute a health metric or other physiological phenomena.

The light sources 614 may operate at the same light wavelength range, or the light sources 614 can operate at different light wavelength ranges. In one example, two light sources may be used rather than the one light source 614 shown. A first of the two light sources may transmit light in the visible wavelength range while a second of the two light sources may emit light in the infrared wavelength range. In some cases, a modulation pattern or sequence may be used to turn the light sources on and off and sample or sense the reflected light. In another example, three light sources may be used rather than the one light source 614 shown. The first of the three light sources in this example may include, for example, a green LED, which may be adapted for detecting blood perfusion in the body of the wearer. The second of the three light sources in this example may include, for example, an infrared LED, which may be adapted to detect changes in water content or other properties of the body. The third of the three light sources in this example may be a similar type or different types of LED element, depending on the sensing configuration.

The bio-sensor or sensors (e.g., PPG) may be used to compute various health metrics or physiological conditions, including, without limitation, a heart rate, a respiration rate, blood oxygenation level, a blood volume estimate, blood pressure, or a combination thereof. In some instances, blood may absorb light more than surrounding tissue, so less reflected light will be sensed by the light receiver 615 of the PPG sensor when more blood is present. The user's blood volume increases and decreases with each heartbeat. Thus, in some cases, a PPG sensor may be configured to detect changes in blood volume based on the reflected light, and one or more physiological conditions or parameters of the user may be determined by analyzing the reflected light. Example physiological conditions include, but are not limited to, heart rate, respiration rate, blood hydration, oxygen saturation, blood pressure, perfusion, and others.

While an example number of light sources 614 and/or light receivers 615 have been described, the number of light sources 614 and/or light receivers 615 may vary in different embodiments. For example, another embodiment may use more than one light receiver 615. Another embodiment may also use fewer or more light sources 614. In particular, in one example, the light receiver 615 may be shared between multiple light sources 614. In one alternative embodiment, two light receivers 615 may be paired with two corresponding light sources 614 to form two bio-sensors. The two bio-sensors (light source 614/light receiver 615 pairs) may be operated in tandem and used to improve the reliability of the sensing operation. For example, output of the two light receivers 615 may be used to detect a pulse wave of fluid (e.g., blood) as it passes beneath the respective light receivers 615. Having two bio-sensor readings taken at different locations along the pulse wave may allow the device to compensate for noise created by, for example, movement of the user, stray light, and other effects.

In some implementations, one or more of the light sources 614 and the light receiver 615 may also be used for optical data transfer with a base or other device. For example, the light receiver 615 may be configured to detect light produced by an external mating device, which may be interpreted or translated into a digital signal. Similarly, one or more of the light sources 614 may be configured to transmit light that may be interpreted or translated into a digital signal by an external device.

Figure 7A:
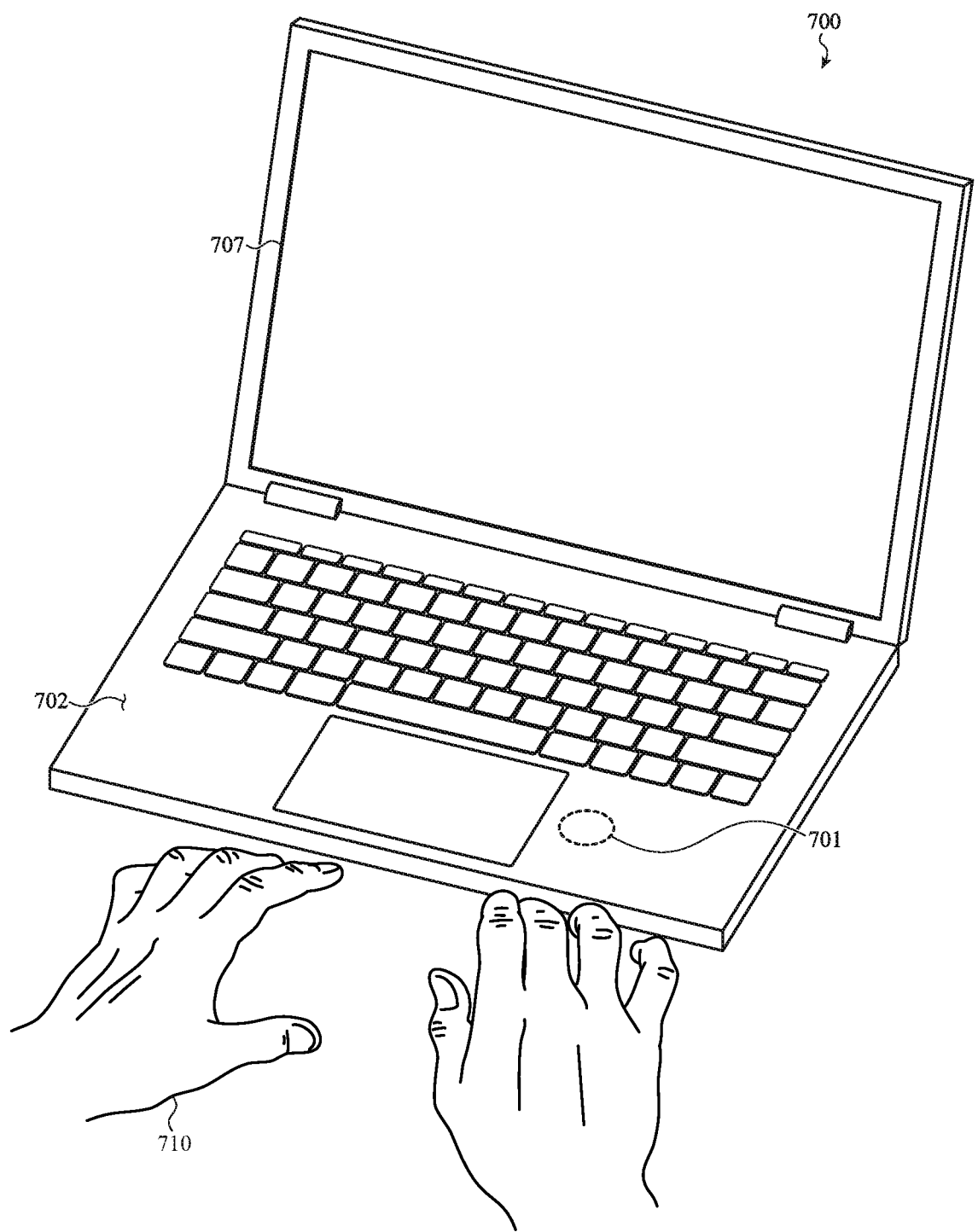
FIG. 7A depicts an example electronic device that is operable to transition from a low power state to an operating state upon detecting a user.
Figure 7B:
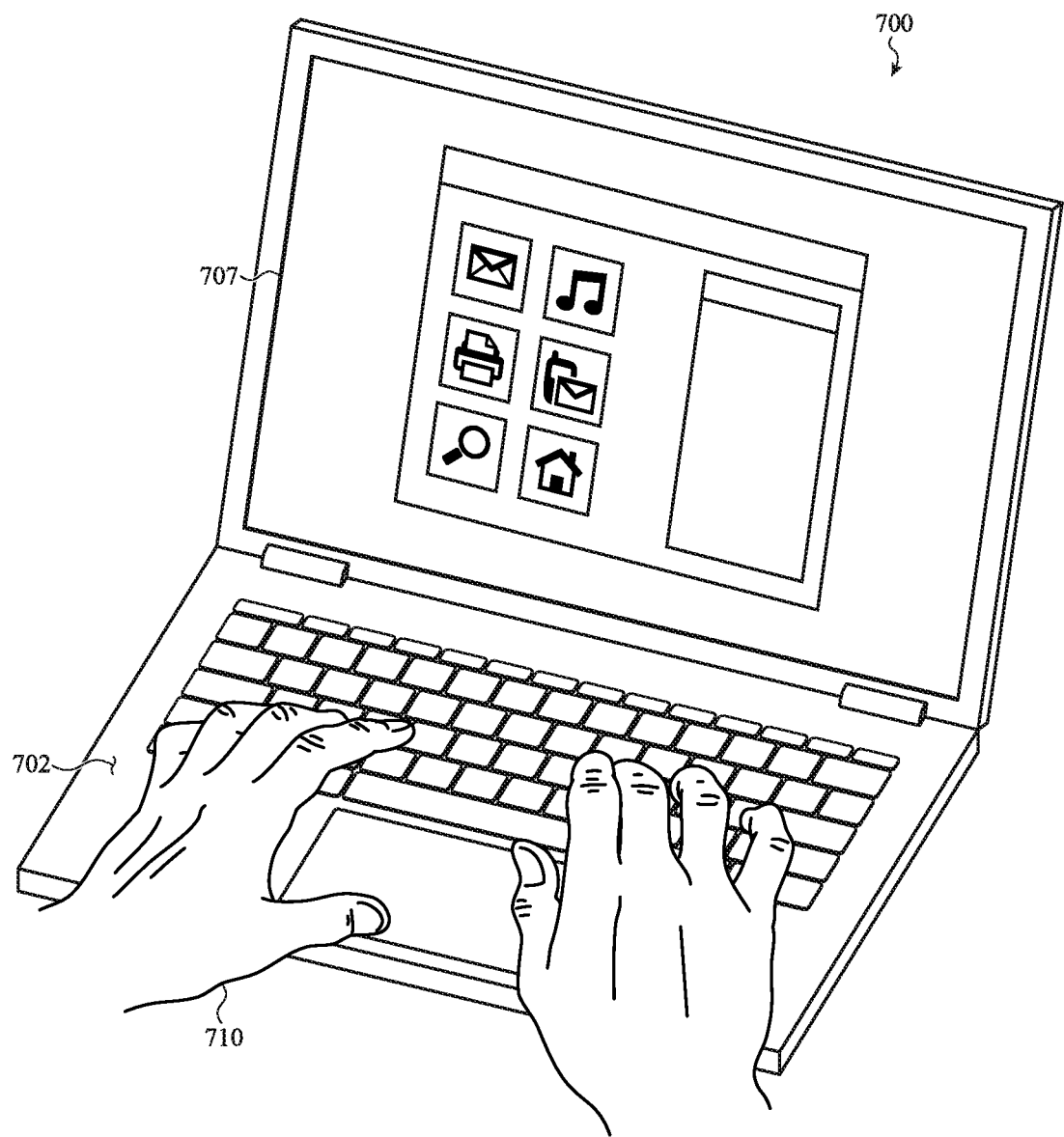
FIG. 7B depicts the example electronic device of FIG. 7A after detection of the user and transition from the low power state to the operating state.

FIGS. 7A-7B depict an example electronic device 700 that is operable to transition from a low power state to an operating state upon detecting a user 710. As illustrated in FIG. 7A, a low power state may be a state where a display 707 is powered off. Powering off the display 707 may conserve power that would be wasted if the user 710 was not using the electronic device 700.

When the electronic device 700 is in the low power state, the electronic device 700 may detect a body part of the user 710 using a bio-sensor operating as a proximity detector or in a proximity-sensing mode within an area 701 of a translucent layer 702. In response, the electronic device 700 may transition from the low power state to the operating state. As a result, the electronic device 700 may power on the display 707, as illustrated in FIG. 7B.

The electronic device 700 may operate in the low power state when the electronic device 700 has been inactive for a period of time. The inactive period of time may be configurable and may include a time ranging from less than a minute to 30 minutes or longer. The electronic device 700 may determine the electronic device 700 is not in use when the sensor does not detect the body part of a user 710. When the electronic device 700 is in the operating state and determines the electronic device 700 is not in use, the electronic device 700 may power off the display 707, as illustrated in FIG. 7A.

Figure 8:
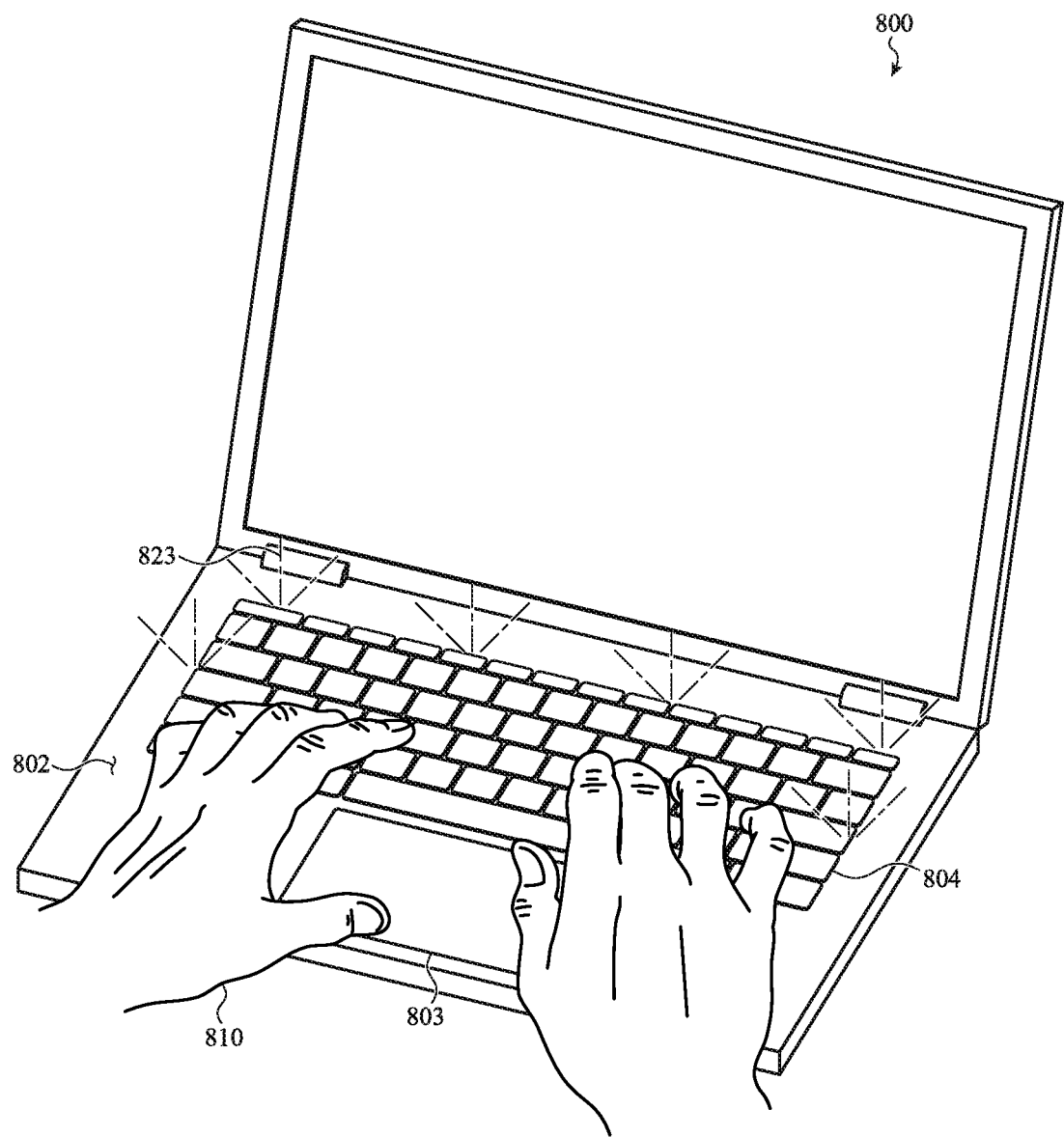
FIG. 8 depicts an example electronic device that is operable to illuminate a keyboard and the trackpad upon detecting a user.

FIG. 8 depicts an example electronic device 800 that is operable to illuminate a keyboard 804 upon detecting a user 810. This may allow the user 810 to better see the keyboard 804, use the electronic device in poorly lit or unlit conditions, and so on. In this example, the electronic device 800 is operable to detect a body part of the user 810 using the bio-sensor operating as a proximity and/or ambient light sensor or in a proximity- or ambient light-sensing mode. The bio-senor may be configured to detect the proximity of the user or an ambient light condition over an area of a translucent layer 802 covered by the body part of the user 810. Upon such a detection, the electronic device 800 may illuminate keyboard 804 and the trackpad 803. As illumination 823 may not be needed when not in use and may be disturbing, such as by illuminating a dark room where the user 810 may be attempting to sleep, this configuration may prevent keyboard 804 illumination 823 when the user 810 does not desire the keyboard 804 illuminated.

Figure 9:
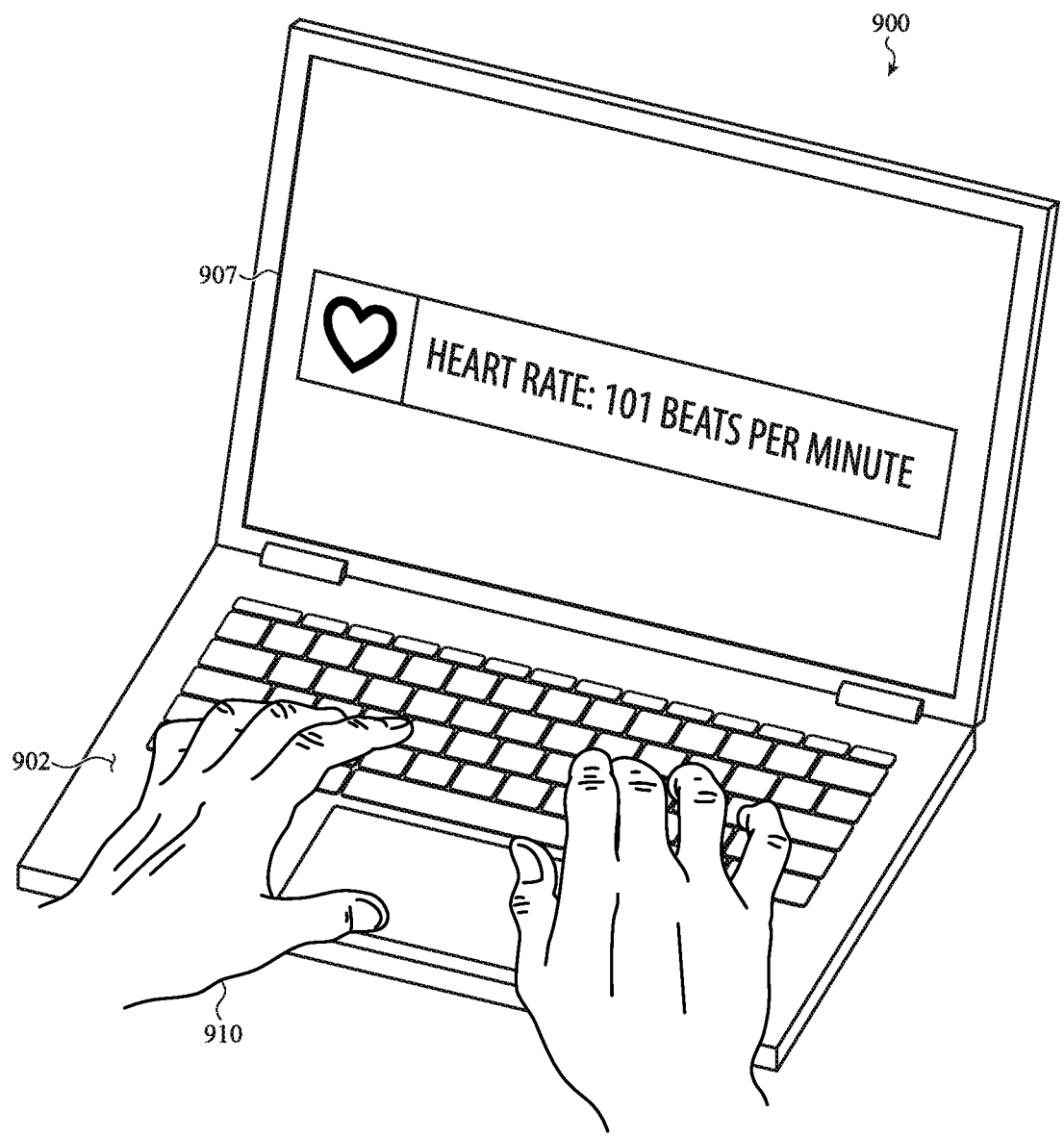
FIG. 9 depicts an example electronic device that is operable to detect and display health information about a user.

FIG. 9 depicts an example electronic device 900 that is operable to detect and display health information about a user 910. In this example, the electronic device 900 is operable to determine a heart rate for the user 910 using a health or other bio-sensor corresponding to an area of a translucent layer 902 covered by a body part of a user 910. The electronic device 900 may then display the determined heart rate for the user 910 on a display 907. In some implementations, the bio-sensor may be used to determine a health metric or physiological condition of the user 910, while the user 910 is typing or otherwise operating the device 900.

Additionally, the electronic device 900 may be able to record the heart rate of the user 910. In this way, the heart rate may be monitored over time. The user's heart rate over time may be compared with the heart rate of other users and/or various other statistical information. For example, the user's heart rate over time may be compared to heart rate data indicating health problems, such as hypertension. The electronic device 900 may display such information, graphically or otherwise, to indicate changes in the user's health, steps the user 910 may take to improve the user's health, comparisons to other people of a similar age and/or other background to indicate the user's relative health, and so on.

In other implementations, the electronic device 900 may monitor the user's heart rate over time to determine satisfaction or frustration levels. For example, a user's heart rate may increase when the user 910 is frustrated. When the electronic device 900 detects the user's heart rate has increased, the electronic device 900 may determine that the user 910 is frustrated and offer help tips regarding an application the user 910 is currently executing on the electronic device 900. Various configurations are possible and contemplated.

Figure 10:
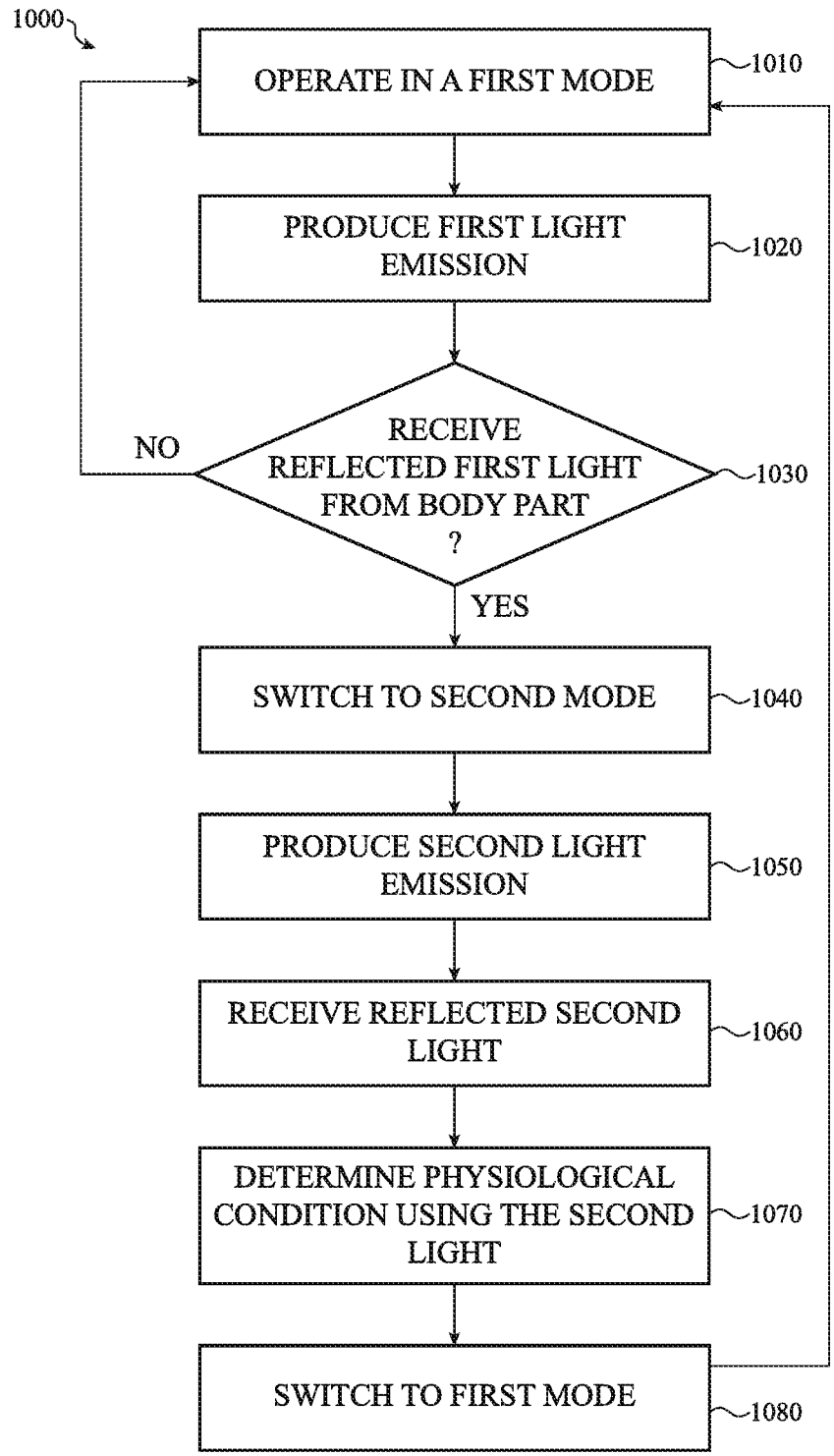
FIG. 10 depicts a flow chart illustrating an example process for sensing a physiological condition or health metric.

FIG. 10 depicts a flow chart illustrating an example method 1000 process for sensing a physiological condition. The example method 1000 may be performed by a device like the example electronic devices 100, 700, 800, 900 of FIGS. 1A-1B and 7A-9.

At 1010, a bio-sensor of a device operates in a first mode. The first mode may be a proximity-sensing mode. As part of operating in the first mode, at 1020, the bio-sensor produces a first light emission or other optical energy through micro-perforations defined in an opaque layer on a translucent layer into a body part of a user. At 1030, the bio-sensor determines whether or not reflected first light from the body part of the user is received through the micro-perforations in the opaque layer on the translucent layer. If the bio-sensor determines reflected first light from the body part of the user is received, this indicates the body part is proximate. As such, the flow proceeds to 1040. Otherwise, the flow returns to 1010 and the bio-sensor continues operating in the first mode.

At 1040, after the bio-sensor may be used to determine that the body part is proximate, the bio-sensor may switch to a second mode. The second mode may be a PPG sensing mode. As part of operating in the second mode, at 1050, the bio-sensor may produce a second light emission or other optical energy through the micro-perforations into the body part. At 1060, the bio-sensor receives the second light reflected from the body part through the micro-perforations.

At 1070, the bio-sensor is used to determine a health metric, physiological condition, bio-information, or other information, using the reflected second light. The flow then returns to 1010 after the bio-sensor switches back to the first mode at 1080.

The bio-sensor may switch between the first and second modes for a variety of reasons. For example, the first and second types of light may be different types of light. In some implementations, the first light may be infrared light and the second light may be visible light (such as red colored light, green colored light, a combination thereof, and so on). As such, the bio-sensor may operate in the first mode using infrared light until the body part is detected because infrared light may not be visible to users. Once the bio-sensor is covered by the body part such that the second light would not be visible, the bio-sensor may switch to the second mode.

By way of another example, the second mode may consume power at a second rate that is greater than a first rate \ the first mode. In various implementations, transmission of the second light may consume more power than transmission of the first light. Thus, the bio-sensor may conserve power by operating in the first mode until the body part is detected so that power is not unnecessarily wasted by operating in the second mode when there is no body part from which to determine a physiological condition of a user.

Although the example method 1000 is illustrated and described as including particular operations performed in a particular order, it is understood that this is an example. In various implementations, various orders of the same, similar, and/or different operations may be performed without departing from the scope of the present disclosure.

For example, the example method 1000 describes transmitting first light in the first mode, second light in the second mode, and switching from the first mode to the second mode when the first light is received reflected back from a body part. However, in some implementations, the bio-sensor may transmit light in the second mode but not the first mode. In such implementations, the bio-sensor may use other information to determine when a body part is proximate. For example, the bio-sensor may monitor a capacitive sensor in the first mode. The capacitive sensor may provide an indication of a changed capacitance when the body part is proximate. When the bio-sensor receives such a signal, the bio-sensor may switch to the second mode and transmit light to determine the physiological condition. Various configurations are possible and contemplated without departing from the scope of the present disclosure.

As described above and illustrated in the accompanying figures, the present disclosure relates to body sensing via translucent layers with opaque layers. An electronic device may optically detect information about a user's body by transmitting light or other optical energy through micro-perforations defined in an opaque layer on a translucent layer and determining what portion of the light is reflected back from the user's body though the micro-perforations. This may allow detection of a variety of different information about the user's body without visible sensors or sensor components. This sensing capability may be incorporated into the housing of an electronic device, such as the area of a laptop computing device around a keyboard and/or trackpad. Examples of sensors that may be implemented in this fashion include, but are not limited to, proximity sensors, infrared distance sensors, ambient light sensors, health sensors, and so on.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not intended to be exhaustive or to limit the embodiments to the precise forms disclosed. It will be apparent to one of ordinary skill in the art that many modifications and variations are possible in view of the above teachings.

For example, features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples.

What is claimed is:

1. A portable electronic device, comprising:
an upper enclosure;
a display positioned within the upper enclosure;
a lower enclosure pivotally coupled to the upper enclosure and comprising:
  a translucent layer defining an external surface; and
  an opaque layer coupled to the translucent layer and defining an array of micro-perforations;
a keyboard positioned within the lower enclosure;
a bio-sensor positioned within the lower enclosure below the array of micro-perforations and comprising:
  a light source operable to transmit light through the array of micro-perforations into a body part of a user; and
  a light receiver operable to receive reflected light from the body part of the user; and
a processing unit, communicably coupled to the light receiver and operable to determine a health metric based on the reflected light.

2. The portable electronic device of claim 1, wherein:
the bio-sensor is positioned along a side of the keyboard; and
the body part is a palm of a hand of the user.

3. The portable electronic device of claim 1, wherein:
the light source is a green LED;
the bio-sensor is configured to detect blood perfusion in the body part of the user; and
the health metric is at least one of: a heart rate, a respiration rate, a blood oxygenation level, a blood volume estimate, or a blood pressure.

4. The portable electronic device of claim 1, wherein:
the light source is an infrared LED; and
the bio-sensor is configured to detect water content of the body part of the user.

5. The portable electronic device of claim 1, wherein the array of micro-perforations are configured to obscure the light source and the light receiver when the bio-sensor is not in operation.

6. The portable electronic device of claim 1, wherein each micro-perforation of the array of micro-perforations is approximately 30-70 microns in diameter and is spaced approximately 80-500 microns apart from an adjacent micro-perforation.

7. The portable electronic device of claim 1, wherein:
the translucent layer comprises glass; and
the opaque layer includes a layer of ink deposited on an internal surface of the translucent layer that is opposite to the external surface.

8. The portable electronic device of claim 1, wherein:
the translucent layer comprises plastic; and
the opaque layer includes a layer of ink deposited on an internal surface of the translucent layer that is opposite to the external surface.

9. The portable electronic device of claim 1, wherein:
the upper enclosure and the lower enclosure define an enclosure of a notebook computer.

10. An electronic device, comprising:
an enclosure having a translucent layer that forms part of an exterior surface of the electronic device;
a keyboard positioned within the enclosure;
an opaque material positioned along an interior surface of the translucent layer and defining an array of micro-perforations;
a bio-sensor positioned within the enclosure and below the array of micro-perforations, the bio-sensor comprising:
  a light source configured to transmit light through the array of micro-perforations;
  a light receiver configured to detect reflected light from a body part exterior to the enclosure; and
  a processing unit operable to determine bio-information based on the reflected light detected by the light receiver.

11. The electronic device of claim 10, wherein:
the light source transmits the light through a first set of micro-perforations in the array of micro-perforations;
the light receiver receives the reflected light through a second set of micro-perforations in the array of micro-perforations;
the first set of micro-perforations extends along a first angle with respect to the exterior surface; and
the second set of micro-perforations extends along a second angle with respect to the exterior surface, the second angle different from the first angle.

12. The electronic device of claim 11, wherein the first set of micro- perforations is angled toward the second set of micro-perforations.

13. The electronic device of claim 10, wherein:
the light source transmits the light through a first set of micro-perforations in the array of micro-perforations;
the light receiver receives the reflected light through a second set of micro-perforations in the array of micro-perforations; and
the first set of micro-perforations extends along a non-perpendicular angle with respect to the exterior surface.

14. The electronic device of claim 10, wherein:
the light source transmits the light through a first set of micro-perforations in the array of micro-perforations;
the light receiver receives the reflected light through a second set of micro-perforations in the array of micro-perforations; and
the second set of micro-perforations extends along a non-perpendicular angle with respect to the exterior surface and blocks light that is not substantially aligned with the non- perpendicular angle.

15. The electronic device of claim 10, wherein the body part absorbs a portion of the light.

16. The electronic device of claim 15, wherein the portion of the light absorbed by the body part depends on a tissue density of the body part.

17. The electronic device of claim 10, wherein: the processing unit is configured to:
operate the light source and the light receiver in a first mode to detect a proximity of the body part with respect to the exterior surface; and
after detecting the body part is proximate to the exterior surface, operate the light source and the light receiver in a second mode to determine a physiological condition of the user.

18. The electronic device of claim 17, wherein:
the light source makes a non-visible light emission when operated in the first mode; and
the light source makes a visible light emission when operated in the second mode.

19. The electronic device of claim 17, wherein determining the physiological condition comprises determining at least one of: a heart rate, a respiration rate, a blood oxygenation level, a blood volume estimate, or a blood pressure.

20. The electronic device of claim 17, wherein determining the physiological condition comprises determining a photoplethysmogram for the user.

* * * * *